US00PP22942P2

(12) United States Plant Patent
Sakazaki

(10) Patent No.: US PP22,942 P2
(45) Date of Patent: Aug. 7, 2012

(54) *CALIBRACHOA* PLANT NAMED 'USCAL66501'

(50) Latin Name: ***Calibrachoa* sp.**
Varietal Denomination: USCAL66501

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 241 days.

(21) Appl. No.: 12/802,245

(22) Filed: Jun. 1, 2010

(51) Int. Cl.
*A01H 5/00* (2006.01)

(52) U.S. Cl. ..... Plt./413

(58) Field of Classification Search ..... Plt./413
See application file for complete search history.

(56) References Cited

U.S. PATENT DOCUMENTS

PP17,678 P2 * 5/2007 Sakazaki ..... Plt./425
PP18,431 P2 * 1/2008 Sakazaki ..... Plt./413

OTHER PUBLICATIONS

UPOV ROM GTITM Computer Database, GTI Jouve Retrieval Software 2011/10 Citation for 'USCAL66501'.*

* cited by examiner

*Primary Examiner* — Wendy C Haas
(74) *Attorney, Agent, or Firm* — C. A. Whealy

(57) ABSTRACT

A new and distinct cultivar of *Calibrachoa* plant named 'USCAL66501', characterized by its compact, mounding and outwardly spreading plant habit; vigorous and freely branching growth habit; dense and bushy appearance; early and freely flowering habit; coral red-colored flowers with greyed purple-colored centers; and good garden performance.

1 Drawing Sheet

Botanical designation: *Calibrachoa* sp.
Cultivar denomination: 'USCAL66501'.

BACKGROUND OF THE INVENTION

The present invention relates to a new and distinct cultivar of *Calibrachoa* plant, botanically known as *Calibrachoa* sp. and hereinafter referred to by the name 'USCAL66501'.

The new *Calibrachoa* plant is a product of a planned breeding program conducted by the Inventor in Higashiomi, Shiga, Japan and Bonsall, Calif. The objective of the breeding program is to create new *Calibrachoa* plants with uniform plant habit, freely branching growth habit, attractive flowers and good garden performance.

The new *Calibrachoa* plant originated from a cross-pollination made by the Inventor on May 7, 2007 in Higashiomi, Shiga, Japan of a proprietary seedling selection of *Calibrachoa* sp. identified as code number CJ07-56, not patented, as the female, or seed, parent with a proprietary seedling selection of *Calibrachoa* sp. identified as code number CJ07-57, not patented, as the male, or pollen, parent. The new *Calibrachoa* plant was discovered and selected by the Inventor as a single flowering plant within the progeny of the stated cross-pollination in a controlled environment in Bonsall, Calif. on May 21, 2008.

Asexual reproduction of the new *Calibrachoa* plant by terminal cuttings in a controlled environment in Bonsall, Calif. since May 23, 2008 has shown that the unique features of this new *Calibrachoa* plant are stable and reproduced true to type in successive generations.

SUMMARY OF THE INVENTION

Plants of the new *Calibrachoa* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'USCAL66501'. These characteristics in combination distinguish 'USCAL66501' as a new and distinct cultivar of *Calibrachoa:*

1. Compact, mounding and outwardly spreading plant habit.
2. Vigorous and freely branching growth habit; dense and bushy appearance.
3. Early and freely flowering habit.
4. Coral red-colored flowers with greyed purple-colored centers.
5. Good garden performance.

The new *Calibrachoa* plant can be compared to plants of the female parent selection. Plants of the new *Calibrachoa* differ primarily from plants of the female parent selection in the following characteristics:

1. Plants of the new *Calibrachoa* are more mounding than and not as creeping as plants of the female parent selection.
2. Plants of the new *Calibrachoa* and the female parent selection differ in flower color as plants of the female parent selection have smaller dark-colored centers.

The new *Calibrachoa* plant can be compared to plants of the male parent selection. Plants of the new *Calibrachoa* differ primarily from plants of the male parent selection in the following characteristics:

1. Plants of the new *Calibrachoa* are more mounding than and not as upright as plants of the male parent selection.
2. Plants of the new *Calibrachoa* and the male parent selection differ in flower color as plants of the male parent selection have peach-colored flowers.

Plants of the new *Calibrachoa* can be compared to plants of the *Calibrachoa* 'USCALI214-1', disclosed in U.S. Plant Pat. No. 18,431. In side-by-side comparisons conducted in Bonsall, Calif., plants of the new *Calibrachoa* differed primarily from plants of 'USCALI214-1' in the following characteristics:

1. Plants of the new *Calibrachoa* had larger flowers than plants of 'USCALI214-1'.
2. Plants of the new *Calibrachoa* and 'USCALI214-1' differed in flower color as plants of 'USCALI214-1' had coral red-colored flowers without darker-colored centers.

Plants of the new *Calibrachoa* can also be compared to plants of the *Calibrachoa* 'USCALI671M', disclosed in U.S. Plant Pat. No. 17,678. In side-by-side comparisons conducted in Bonsall, Calif., plants of the new *Calibrachoa* differed from plants of 'USCALI671M' in the following characteristics:

1. Plants of the new *Calibrachoa* had larger flowers than plants of 'USCALI671M'.
2. Plants of the new *Calibrachoa* and 'USCALI671M' differed in flower color as plants of 'USCALI671M' had peach-colored flowers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet comprises a side perspective view of a typical flowering plant of 'USCAL66501' grown in a container.

The photograph at the top of the sheet comprises a close-up of a typical flowering plant of 'USCAL66501'.

DETAILED BOTANICAL DESCRIPTION

The aforementioned photographs and following observations, measurements and values describe plants grown during the spring in 15-cm containers in a polyethylene-covered greenhouse in Bonsall, Calif. During the production of the plants, day temperatures ranged from 18° C. to 32° C., night temperatures ranged from 14° C. to 18° C. and light levels ranged from 7,000 to 10,000 foot-candles. Plants were pinched one time and were eight weeks old when the photographs and description were taken. In the following description, color references are made to The Royal Horticultural Society Colour Chart, 2007 Edition, except where general terms of ordinary dictionary significance are used.

Botanical classification: *Calibrachoa* sp. 'USCAL66501'.

Parentage:

*Female, or seed, parent*.—Proprietary seedling selection of *Calibrachoa* sp. identified as code number CJ07-56, not patented.

*Male, or pollen, parent*.—Proprietary seedling selection of *Calibrachoa* sp. identified as code number CJ07-57, not patented.

Propagation:

*Type*.—By terminal cuttings.

*Time to initiate roots, summer*.—About four days at temperatures ranging from 17° C. to 29° C.

*Time to initiate roots, winter*.—About six days at temperatures ranging from 17° C. to 21° C.

*Time to produce a rooted plant, summer*.—About 22 days at temperatures ranging from 17° C. to 29° C.

*Time to produce a rooted plant, winter*.—About 25 days at temperatures ranging from 17° C. to 21° C.

*Root description*.—Medium in thickness, fibrous; white in color.

*Rooting habit*.—Freely branching; moderately dense.

Plant description:

*Plant and growth habit*.—Compact, mounding and outwardly spreading plant habit; freely branching habit with about six to seven lateral branches; pinching enhances branching; vigorous, dense and bushy growth habit.

*Plant height*.—About 13.5 cm.

*Plant diameter*.—About 46 cm.

Lateral branch description:

*Length*.—About 21 cm.

*Diameter*.—About 2 mm.

*Internode length, vegetative*.—About 4 mm.

*Internode length, reproductive*.—About 1.2 cm.

*Strength*.—Strong.

*Aspect*.—Initially upright to outwardly spreading.

*Texture*.—Pubescent.

*Color*.—Close to 146C.

Foliage description:

*Arrangement*.—Before flowering, alternate, simple; after flowering, opposite, simple.

*Length*.—About 3.4 cm.

*Width*.—About 1.3 cm.

*Shape*.—Elliptical.

*Apex*.—Broadly acute.

*Base*.—Attenuate.

*Margin*.—Entire.

*Texture, upper and lower surfaces*.—Pubescent.

*Venation pattern*.—Pinnate; arcuate.

*Color*.—Developing leaves, upper surface: Close to 146A. Developing leaves, lower surface: Close to 146B. Fully expanded leaves, upper surface: Close to 137B; venation, close to 146B. Fully expanded leaves, lower surface: Close to 147B; venation, close to 146C.

*Petiole*.—Length: About 4 mm. Diameter: About 3 mm. Texture, upper and lower surfaces: Pubescent. Color, upper and lower surfaces: Close to 146C.

Flower description:

*Flower arrangement and habit*.—Single slightly asymmetrical salverform flowers arising from leaf axils; freely flowering habit with usually about 16 open flowers and flower buds per lateral branch; flowers face upright and outwardly.

*Fragrance*.—None detected.

*Natural flowering season*.—Early flowering habit, plants of the new *Calibrachoa* begin flowering about six weeks after planting; plants flower continuously from spring though the autumn in California.

*Flower longevity*.—Individual flowers last about five to seven days on the plant; flowers persistent.

*Flower diameter*.—About 3.3 cm by 3.5 cm.

*Flower length (height)*.—About 2.8 cm.

*Flower throat diameter*.—About 6 mm by 8 mm.

*Flower tube diameter, base*.—About 2 mm.

*Flower tube length*.—About 1.9 cm.

*Flower bud*.—Shape: Elongated oblong. Length: About 2.7 cm. Diameter: About 1 cm. Color: Close to 180D.

*Corolla*.—Arrangement: Five petals fused at the base and opening into a flared trumpet. Petal lobe length (from throat): About 1.2 cm. Petal lobe width: About 1.6 cm. Petal shape: Roughly cordate. Petal apex: Slightly emarginate. Petal margin: Entire. Petal texture, upper surface: Smooth, glabrous; velvety. Petal texture, lower surface: Pubescent. Throat texture: Smooth, glabrous. Tube texture: Pubescent. Color: Petal lobe, when opening, upper surface: Close to 53C. Petal lobe, when opening, lower surface: Close to 181C. Petal lobe, fully opened, upper surface: Close to 37A to 37B; towards the throat, close to 53A and closer to the throat, close to 187B; color of outer petal lobes becoming closer to 179D with development; venation, close to 47A. Petal lobe, fully opened, lower surface: Close to 180C; color does not fade with development; venation, close to N199A. Throat: Close to 7A; venation, close to 152B. Tube: Close to 1A; venation, close to 152B.

*Calyx*.—Arrangement: One star-shaped calyx tube with five sepals in a single whorl and fused at the base. Sepal length: About 1.2 cm. Sepal width: About 3 mm. Sepal shape: Ligulate. Sepal apex: Acute. Sepal margin: Entire. Sepal texture, upper and lower surfaces: Pubescent. Color, upper and lower surfaces: Close to 146A.

*Peduncles*.—Length: About 1.8 cm to 2 cm. Diameter: About 1 mm Angle: About 30° to 45° from stem axis. Strength: Strong. Texture: Pubescent. Color: Close to 146B.

*Reproductive organs*.—Stamens: Quantity: About five per flower. Filament length: About 1 cm. Filament color: Close to 145D. Anther shape: Oval. Anther length: About 1 mm. Anther color: Close to 8A. Pollen amount: Scarce. Pollen color: Close to 7A. Pistils: Quantity: One per flower. Pistil length: About 1.2 cm. Style length: About 8 mm. Style color: Close to 145A. Stigma shape: Oval. Stigma color: Close to 137B. Ovary color: Close to 146C. Seed/fruit: Seed and fruit development have not been observed on plants of the new *Calibrachoa*.

Garden performance: Plants of the new *Calibrachoa* have been observed to have good garden performance and tolerate wind, rain and temperatures ranging from about 1° C. to about 40° C.

Pathogen/pest resistance: Plants of the new *Calibrachoa* have not been observed to be resistant to pathogens and pests common to *Calibrachoa*.

It is claimed:

1. A new and distinct *Calibrachoa* plant named 'USCAL66501' as illustrated and described.

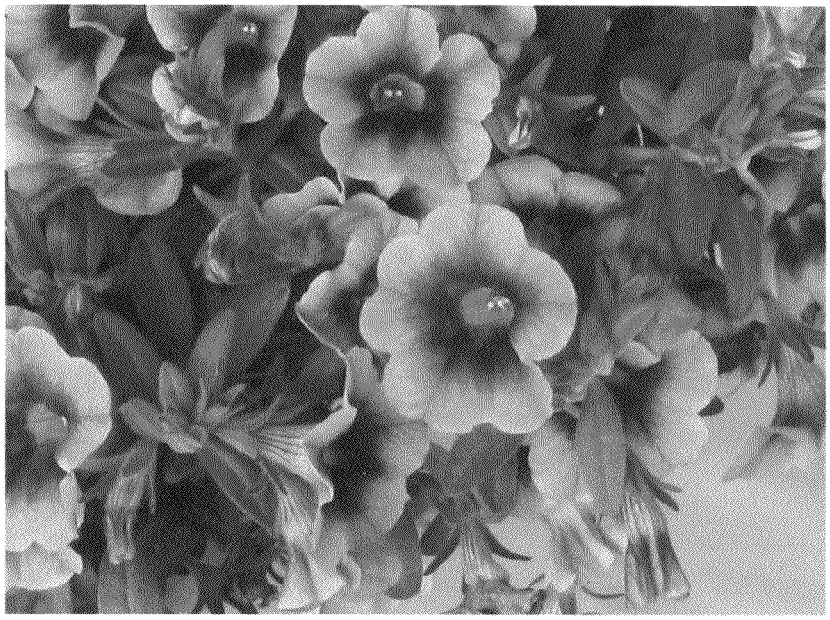
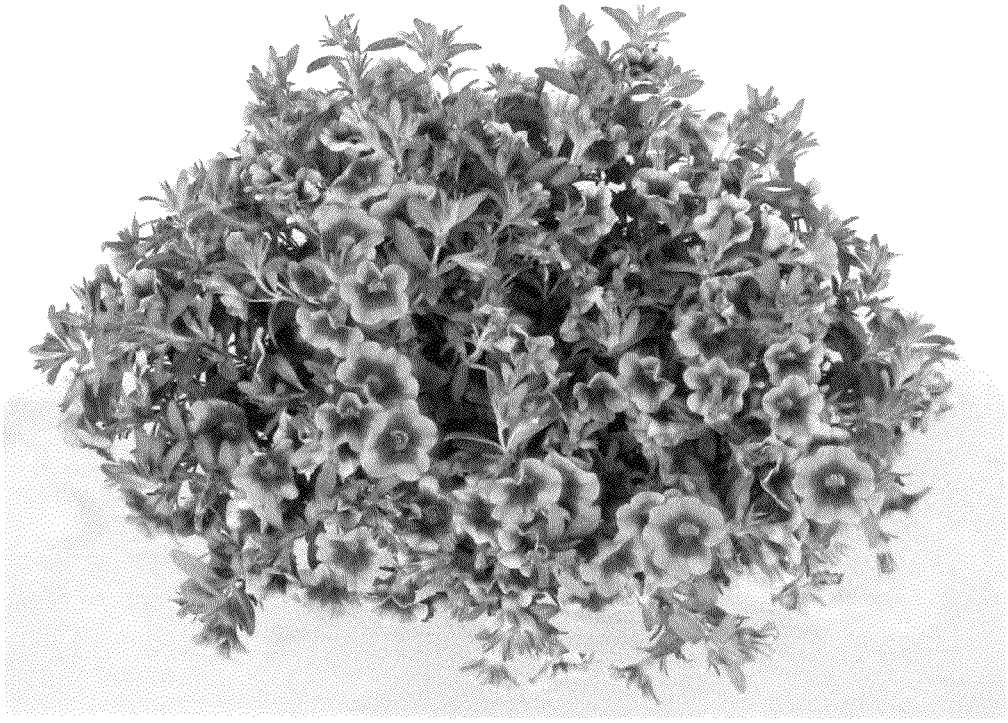

* * * * *